United States Patent
Brewer

(10) Patent No.: US 12,232,935 B2
(45) Date of Patent: Feb. 25, 2025

(54) ORTHOPEDIC CAST SPLITTER APPARATUS AND RELATED METHODS FOR SPLITTING A CAST

(71) Applicant: Colorado State University Research Foundation, Fort Collins, CO (US)

(72) Inventor: Kevin Brewer, Nunn, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 908 days.

(21) Appl. No.: 17/367,191

(22) Filed: Jul. 2, 2021

(65) Prior Publication Data

US 2022/0000674 A1 Jan. 6, 2022

Related U.S. Application Data

(60) Provisional application No. 63/047,562, filed on Jul. 2, 2020.

(51) Int. Cl.
*A61F 13/04* (2006.01)
*A61F 15/00* (2006.01)

(52) U.S. Cl.
CPC ............ *A61F 13/041* (2013.01); *A61F 15/00* (2013.01)

(58) Field of Classification Search
CPC ........ A61F 13/043; A61F 15/00; A61F 13/04; A61F 13/041
USPC ...................................................... 606/105.5
See application file for complete search history.

(56) References Cited

U.S. PATENT DOCUMENTS

| | | | | |
|---|---|---|---|---|
| 3,426,752 A | * | 2/1969 | Laico | A61F 15/02 606/53 |
| 3,705,581 A | * | 12/1972 | Drake | A61F 15/02 606/53 |
| 6,874,217 B2 | | 4/2005 | Ploeger et al. | |
| 7,076,850 B2 | | 7/2006 | Ploeger et al. | |

OTHER PUBLICATIONS

Lisle 29100 Quick Quad Pad Spreader, https:/ /www.amazon.com/Lisle-29100-Quick-Quad-Spreader/dp/B005GLOCKA/ref=asc df B005GLOCKA/Ptag=hyprod-20&linkCode=df0&hvadid=312094794461&hypos=1o2&hvnetw=g&hvrand=10782357166729003909&hypone=&hvptwo=&hvqmt=&hvdev=c& hvdvcmdl=&hvlocint=&hvlocphy=9028897&hvtargid=pla-392689279577&psc=1&tag=&ref=&adgrpid=62497261819&hvpone=&hvptwo=&hvadid=312094794461&hvpos=1o2&hvnetw=g&hvrand= 10782357166729003909&hvqmt=&hvdev=c&hvdvcmdl=&hylocint=&hvlocphy=9028897&hytargid=pla-392689279577, accessed Jun. 13, 2019.

* cited by examiner

*Primary Examiner* — Kevin T Truong
*Assistant Examiner* — Diana Jones
(74) *Attorney, Agent, or Firm* — Meunier Carlin & Curfman LLC

(57) ABSTRACT

An orthopedic cast splitter apparatus for splitting an orthopedic cast may include a frame, a handle pivotally coupled to the frame, a drive rod configured to translate relative to the frame, and a jaws. The jaws may include a first plate coupled to the frame, and a second plate coupled to the drive rod and extending parallel to the first plate, with the second plate being configured to translate relative to the first plate. The jaws also may include a first tooth removably coupled to the first plate and extending beyond an end of the first plate, and a second tooth removably coupled to the second plate and extending beyond an end of the second plate, with (Continued)

the first tooth and the second tooth being configured to be inserted within a fissure formed in the orthopedic cast.

20 Claims, 7 Drawing Sheets

ORTHOPEDIC CAST SPLITTER APPARATUS AND RELATED METHODS FOR SPLITTING A CAST

CROSS-REFERENCE TO RELATED APPLICATIONS

This application claims priority to and the benefit of U.S. Provisional Patent Application No. 63/047,562, filed on Jul. 2, 2020, the disclosure of which is expressly incorporated herein by reference in its entirety.

FIELD OF THE DISCLOSURE

The present disclosure relates generally to devices and methods for removing a cast from a subject and more particularly to an orthopedic cast splitter apparatus and related methods for splitting a cast to facilitate removal of the cast from a subject.

BACKGROUND OF THE DISCLOSURE

An orthopedic cast, or cast, is a shell routinely made of plaster or fiberglass. The cast encases a limb to stabilize and hold anatomical structures, e.g., broken bones, in place for healing. Once healing is confirmed, the cast is typically removed, first by perforation using a cast saw, an oscillating saw designed to cut rigid materials while not harming soft tissue. Subsequently, a cast splitter is inserted into the fissure and manually spread apart, pursuant the ability of the operator to sufficiently open the device.

The foremost common example of an orthopedic cast splitter resembles a set of pliers. These cast splitters have a set of handles pivotally connected by a rivet, with a set of jaws integrally formed at the opposite end of the handles. The jaws of these cast splitters generally differ in regard to the number of teeth therein, but are functionally identical; with the jaws in a closed position, the teeth are inserted within the fissure of the cast, wherein the operator must spread the ends apart to crack the cast open. The teeth thusly pry open the cast with much exertion on the part of the operator. Some modifications have been made with respect to these common orthopedic cast splitters, in that instead of spreading the device apart, an operator can squeeze the handle together, again resulting in cast splitting.

Both renditions of cast splitters are equally cumbersome to operate as the force required to crack the orthopedic cast are often great enough to require both hands of the operator. Furthermore, the cast can only be spread as wide as the handles are pivotally capable—leaving a more dexterous tool to be desired by the operator. Fundamentally, a cast splitter capable of cracking an orthopedic cast, operable with a minimal amount of force, would be advantageous.

SUMMARY OF THE DISCLOSURE

The present disclosure is directed to an orthopedic cast splitter apparatus designed and fabricated to be inserted within a fissure of an orthopedic cast, wherein operation of a manual drive mechanism effecting movement in the forward axial direction results in orthopedic cast splitting. Various aspects of an orthopedic cast splitter apparatus and related methods for splitting a cast to facilitate removal of the cast from a subject are provided herein.

In one aspect, an orthopedic cast splitter apparatus for splitting an orthopedic cast is provided. The orthopedic cast splitter apparatus may include a frame, a handle pivotally coupled to the frame, a drive rod configured to translate relative to the frame, and a jaws. The jaws may include a first plate coupled to the frame, and a second plate coupled to the drive rod and extending parallel to the first plate, with the second plate being configured to translate relative to the first plate. The jaws also may include a first tooth removably coupled to the first plate and extending beyond an end of the first plate, and a second tooth removably coupled to the second plate and extending beyond an end of the second plate, with the first tooth and the second tooth being configured to be inserted within a fissure formed in the orthopedic cast.

In some embodiments, the handle may be configured to pivot within a central plane defined by the frame, the first plate may extend in a lateral direction perpendicular to the central plane, the second plate may extend in the lateral direction, the first plate may extend in the lateral direction beyond an end of the first plate, and the second plate may extend in the lateral direction beyond an end of the second plate. In some embodiments, the first tooth may be removably coupled to the first plate via one or more first fasteners extending through one or more holes defined in the first tooth and one or more holes defined in the first plate, and the second tooth may be removably coupled to the second plate via one or more second fasteners extending through one or more holes defined in the second tooth and one or more holes defined in the second plate. In some embodiments, the first plate may be rigidly coupled to the frame, and the second plate may be rigidly coupled to the drive rod.

In some embodiments, the first tooth and the second tooth each may include a base portion and a tip portion. The base portion may be disposed between the first plate and the second plate, and the base portion may include a first planar surface and a second planar surface disposed opposite one another and extending parallel to one another. The tip portion may extend beyond the end of the first plate and the end of the second plate, and the tip portion may include a third planar surface and a curved surface disposed opposite one another. The third planar surface may extend parallel to the first planar surface and the second planar surface and may be configured to engage the orthopedic cast along the fissure. The curved surface may be configured to ease insertion within the fissure. In some embodiments, the third planar surface of the first tooth may be disposed opposite the third planar surface of the second tooth, and the curved surface of the first tooth may be disposed opposite the curved surface of the second tooth.

In some embodiments, the jaws may be configured to move between a closed position, in which the first tooth and the second tooth are aligned with one another in a common plane, and an open position in which the first tooth and the second tooth are spaced apart from one another in a direction perpendicular to the common plane. In some embodiments, the jaws also may include a third tooth removably coupled to the first plate or the second plate, and the third tooth may be aligned with the first tooth and the second tooth in the common plane when the jaws is in the closed position.

In some embodiments, the orthopedic cast splitter apparatus also may include a bar extending parallel to the drive rod and configured to maintain an orientation of the second plate relative to the first plate as the second plate translates relative to the first plate. In some embodiments, the bar may be coupled to the drive rod, and the bar may engage an opening defined in the first plate and an opening defined in the second plate. In some embodiments, the bar may be rigidly coupled to the second plate, and the bar may engage an opening defined in the first plate.

In another aspect, an orthopedic cast splitter apparatus for splitting an orthopedic cast is provided. The orthopedic cast splitter apparatus may include a frame, a handle pivotally coupled to the frame and configured to pivot within a central plane defined by the frame, a drive rod configured to translate relative to the frame, and a jaws. The jaws may include a first plate coupled to the frame and extending in a lateral direction perpendicular to the central plane, and a second plate coupled to the drive rod and extending in the lateral direction, with the second plate being configured to translate relative to the first plate. The jaws also may include a first tooth coupled to the first plate and extending in the lateral direction beyond an end of the first plate, and a second tooth coupled to the second plate and extending in the lateral direction beyond an end of the second plate, with the first tooth and the second tooth being configured to be inserted within a fissure formed in the orthopedic cast.

In some embodiments, the first plate may be rigidly coupled to the frame, the second plate may be rigidly coupled to the drive rod, the first tooth may be removably coupled to the first plate, and the second tooth may be removably coupled to the second plate.

In some embodiments, the first tooth and the second tooth each may include a base portion and a tip portion. The base portion may be disposed between the first plate and the second plate, and the base portion may include a first planar surface and a second planar surface disposed opposite one another and extending parallel to one another. The tip portion may extend beyond the end of the first plate and the end of the second plate, and the tip portion may include a third planar surface and a curved surface disposed opposite one another. The third planar surface may extend parallel to the first planar surface and the second planar surface and may be configured to engage the orthopedic cast along the fissure. The curved surface may be configured to ease insertion within the fissure.

In some embodiments, the orthopedic cast splitter apparatus also may include a bar extending parallel to the drive rod and configured to maintain an orientation of the second plate relative to the first plate as the second plate translates relative to the first plate. In some embodiments, the bar may be coupled to the drive rod, and the bar may engage an opening defined in the first plate and an opening defined in the second plate. In some embodiments, the bar may be rigidly coupled to the second plate, and the bar may engage an opening defined in the first plate.

In yet another aspect, a method for splitting an orthopedic cast is provided. The method may include providing an orthopedic cast splitter apparatus that includes a frame, a handle pivotally coupled to the frame and configured to pivot within a central plane defined by the frame, a drive rod configured to translate relative to the frame, and a jaws. The jaws may include a first plate coupled to the frame and extending in a lateral direction perpendicular to the central frame, and a second plate coupled to the drive rod and extending in the lateral direction, with the second plate being configured to translate relative to the first plate. The jaws also may include a first tooth coupled to the first plate and extending in the lateral direction beyond an end of the first plate, and a second tooth coupled to the second plate and extending in the lateral direction beyond an end of the second plate. The method also may include inserting the first tooth and the second tooth within a fissure formed in the orthopedic cast, and pivoting the handle relative to the frame such that the second plate translates relative to the first plate, thereby increasing a size of the fissure.

In some embodiments, the first tooth may be removably coupled to the first plate, and the second tooth may be removably coupled to the second plate. In some embodiments, the method also may include maintaining, via a bar of the orthopedic cast splitter apparatus extending parallel to the drive rod, an orientation of the second plate relative to the first plate as the second plate translates relative to the first plate.

These and other aspects and improvements of the present disclosure will become apparent to one of ordinary skill in the art upon review of the following detailed description when taken in conjunction with the several drawings and the appended claims.

Figure 1:
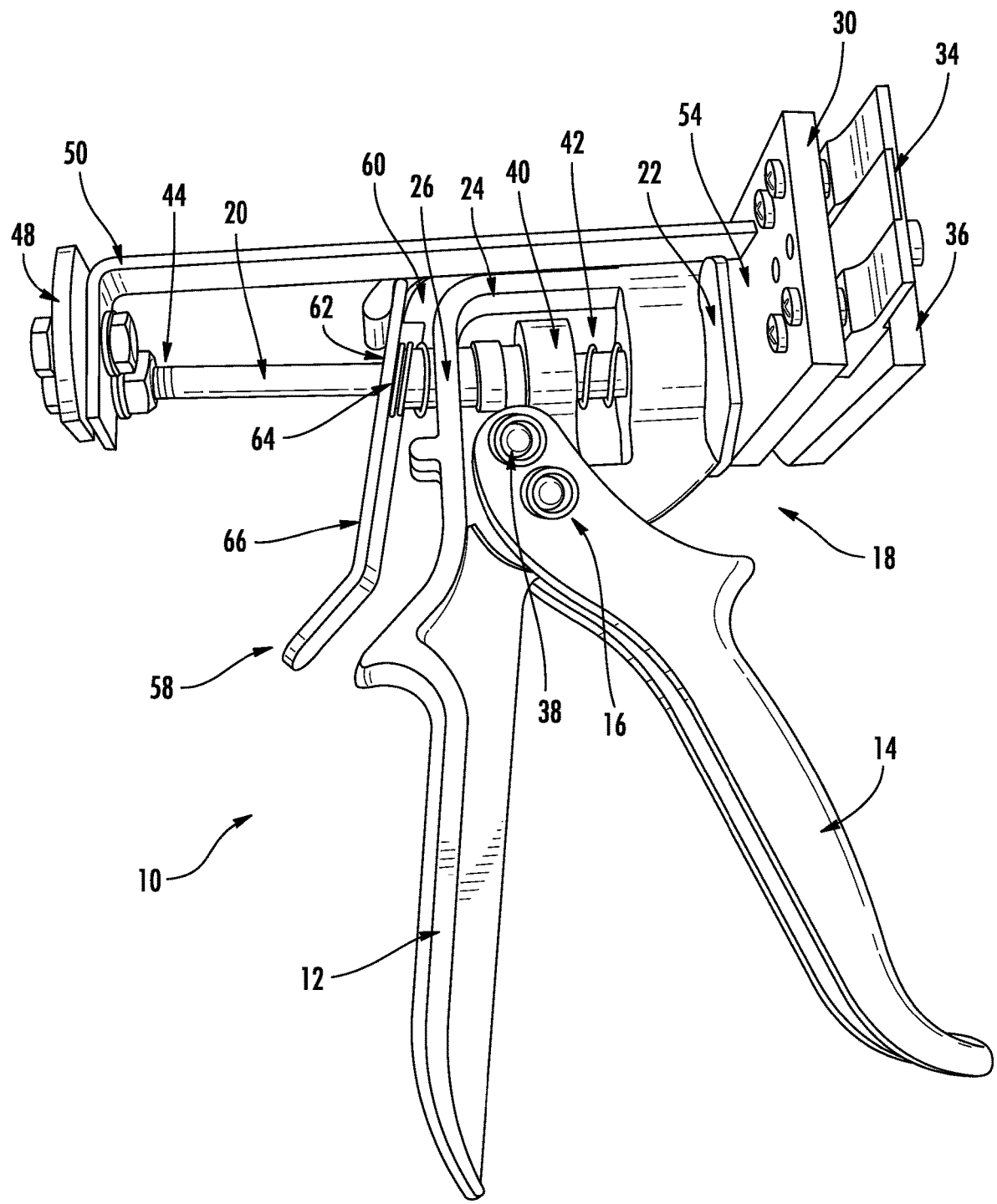
FIG. 1 illustrates a right-facing side view of an orthopedic cast splitter apparatus, in accordance with embodiments of this disclosure.

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The use of the same reference numerals indicates similar, but not necessarily the same or identical components. Different reference numerals may be used to identify similar components. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

While the subject matter disclosed herein is amenable to various modifications and alternate forms, specific embodiments have been shown by way of example. The present disclosure, however, is not limited to the particular embodiments described. On the contrary, the disclosure is intended to cover all modifications, equivalents, and alternatives falling within the ambit of the subject matter disclosed herein.

As used herein, the terms "lower," "upper," "upward," "downward," and/or similar directional terms are used to refer to the specific features with respect to which the terms are used. Such terms are characterized in the context of the illustrations for clarity and to describe relative orientations of features with respect to other features, and are not intended to imply any particular orientation of the apparatus, or absolute (or preferred) orientations of features thereof.

DETAILED DESCRIPTION OF THE DISCLOSURE

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other embodiments and details that, although not specifically described here, are within the scope and spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, components, or features have not been described in detail so as not to unnecessarily obscure aspects of the embodiments.

Overview

Embodiments of an orthopedic cast splitter apparatus may include a frame pivotally connected to a trigger handle. As described below, a top end of the frame may extend above the trigger handle and may be coupled to a fixed plate, and a drive rod may slidably extend through the top end of the frame and the fixed plate. The drive rod ultimately may be connected to an advance plate on the opposing side of the fixed plate. The trigger handle may be positioned to engage an actuator housed within the frame and drive the advance plate along an axis parallel to the drive rod. Continuous actuation of the trigger handle may incrementally engage the drive rod to push the advance plate further from the adjacent fixed plate. The advance plate and the fixed plate together, may make up a set of plates functioning as a jaws of the orthopedic cast splitter apparatus. The jaws may have a set of teeth protruding perpendicular to the drive rod, and the set of teeth may allow for insertion of the orthopedic cast splitter apparatus within a fissure of an orthopedic cast. The overall operation of the manual drive mechanism effecting movement in the forward axial direction results in orthopedic cast splitting.

The orthopedic cast splitter apparatus described herein advantageously may be used to facilitate removal of a cast from a living subject, including animals and humans. Although various applications of the orthopedic cast splitter apparatus described herein may be envisioned, the apparatus may be particularly well suited for veterinary applications, especially for use with large animals, such as horses and the like. In veterinary medicine, the limbs of large animals are quite robust, and thus casts constructed for such animals may be inherently more difficult to remove. For example, the forces applied to split a cast used for a large animal may be far greater that applications involving a small animal or a human patient. Moreover, in contrast to the relative ease with which the relevant limb of a small animal or a human may be moved and oriented to facilitate cast removal, the user may need greater flexibility in orienting removal tools relative to the limb while still maintaining desired visualization of the cast. According to various embodiments, the orthopedic cast splitter apparatus may address these particular challenges as well as the shortcomings of existing cast removal tools discussed above.

Still other aspects, benefits, and advantages of the orthopedic cast splitter apparatus and related methods provided herein over existing technology will be appreciated by those of ordinary skill in the art from the following description and the appended drawings.

Example Embodiments of an Orthopedic Cast Splitter

FIG. 1 illustrates a right facing side view of an orthopedic cast splitter apparatus 10, in accordance with embodiments of this disclosure. As shown in FIG. 1, an orthopedic cast splitter apparatus 10 may include a frame 12 pivotally connected by a pivot pin 16 to a trigger handle 14. The pivot pin 16 may be a rivet, screw, bolt, or any other equivalent fastener as known in the art. A top end 18 of the frame 12, having a leading end 22 and a rear end 26, may extend above the trigger handle 14. The top end 18 of the frame 12 may house a drive rod 20. The drive rod 20, having a first end 44 protruding beyond the rear end 26, may slidably extend through a cavity 24, and through the leading end 22 of the frame 12. The cavity 24 may be any shape, e.g., regular, irregular or any shape. A second end 46 (see FIG. 3) of the drive rod 20 may continue from the leading end 22 and protrude through a first opening 28 (see FIG. 5) of a first end 84 (see FIG. 5) of a fixed plate 30, and the second end 46 of the drive rod 20 may be coupled to an advance plate 36. In some embodiments, the second end 46 of the drive rod 20 may protrude through a first end 32 (see FIG. 5) of the advance plate 36 and couple to an outside surface 78 (see FIG. 3) of the advance plate 36. In further embodiments, the drive rod 20 may be coupled to the first end 32 of an inside surface 34 of the advance plate 36. An outside surface 54 of the fixed plate 30 may be coupled to the leading end 22 of the frame 12, having congruent openings to which the drive rod 20 may extend. Within the cavity 24, the drive rod 20 may be encompassed by an actuator 40 and a first actuator spring 42, and the trigger handle 14 may engage the actuator through a drive pin 38, compressing the first actuator spring 42, and subsequently sliding the drive rod 20 in a forward axial direction displacing the advance plate 36 from the fixed plate 30. In other embodiments, the actuator and actuator spring configuration may consist of a series of actuators and actuator springs to optimally displace the advance plate in a forward axial direction as previously described herein.

In some embodiments, the first end 44 of the drive rod 20, extending beyond the rear end 26 of the frame 12, may be coupled to a slide bar 50, positioned above and running parallel to the drive rod 20, by a connecting bracket 48. The slide bar 50 may protrude above the top end 18 of the frame 12 and through a second opening 52 (see FIG. 3) of the fixed plate 30 and rest adjacent the inside surface 34 of the advance plate 36. The slide bar 50 and the drive rod 20 may evenly displace the advance plate 36 from the fixed plate 30 simultaneously, in response to actuation of the trigger handle 14. In some embodiments, the slide bar 50 may rest within a notch 80 (see FIG. 3) as to assist in proper alignment of the advance plate 36. Components, as discussed herein, may be coupled together in a variety of ways, including but not limited to rivets, screws, bolts or any other fastener as is known in the art. In some embodiments, components may be combined and constructed as one component capable of multiple features as described herein, and in other embodiments, components may be constructed as several individual components and coupled to operate as the components described herein.

In some embodiments, a lock and release lever 58 may be coupled to a first surface 60 of the rear end 26 of the frame 12. The lock and release lever 58 may have a first opening 62 that permits the drive rod 20 to extend through the lock and release lever 58, beyond the rear end 26, and to the connecting bracket 48. Between the lock and release lever 58 and the rear end 26 of the frame 12, a locking spring 64 may be provided. When the trigger handle 14 actuates the drive rod 20 in a forward axial direction (as previously described herein), the lock and release lever 58 may lock the progression of the drive rod 20. Each subsequent actuation of the trigger handle 14, may incrementally extend the advance plate 36 further from the fixed plate 30. The progression of the advance plate 36 may be held by the lock and release lever 58 between each actuation, allowing forward progress to continue at the pace of the operator. The lock and release lever 58 may be unlocked by applying pressure on an outside surface 66 of the lock and release lever 58, consequently releasing the locking spring 64, and allowing the drive rod 20 to travel in a backward axial direction, thereby bringing the advance plate 36 back into a closed position.

Figure 2:
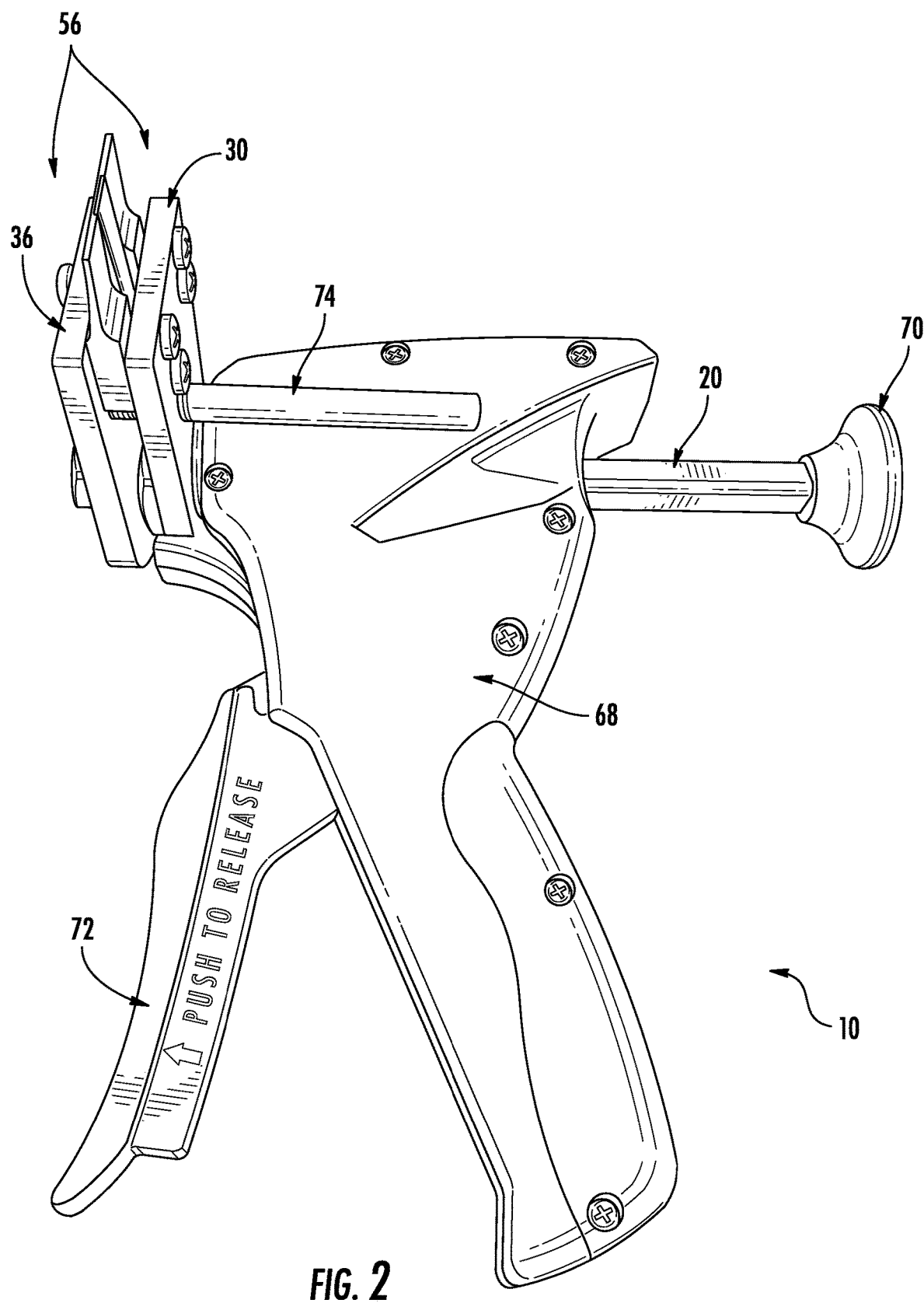
FIG. 2 illustrates a left-facing side view of an orthopedic cast splitter apparatus, in accordance with embodiments of this disclosure.

FIG. 2 illustrates a left facing side view of an orthopedic cast splitter apparatus 10, in accordance with embodiments of this disclosure. As shown in FIG. 2, the frame and actuation components (as described herein) of the orthopedic cast splitter apparatus 10 may be housed within a case 68. The drive rod 20, extending beyond the rear end 26 (not shown) of the frame 12 (not shown), may end in a plunger 70. The plunger 70 may be pulled in a backward axial direction once the locking spring is released, allowing the orthopedic cast splitter apparatus 10 to be reset to a closed position, in which a set of plates 56 may be abutting.

In other embodiments, the orthopedic cast splitter apparatus 10 (as shown in FIG. 2) may have a combined lock and release trigger handle 72. Actuation of the drive rod 20 herein, is systematically similar as previously described herein; release of the drive rod 20 however, is done by pushing forward on the lock and release trigger handle 72 (as indicated in FIG. 2).

In further embodiments, the orthopedic cast splitter apparatus 10, may have an alignment bar 74 independent from the drive rod 20. The alignment bar 74 may permit the advance plate 36 uniform movement from fixed plate 30 as the set of plates 56 operate to split an orthopedic cast.

Figure 3:
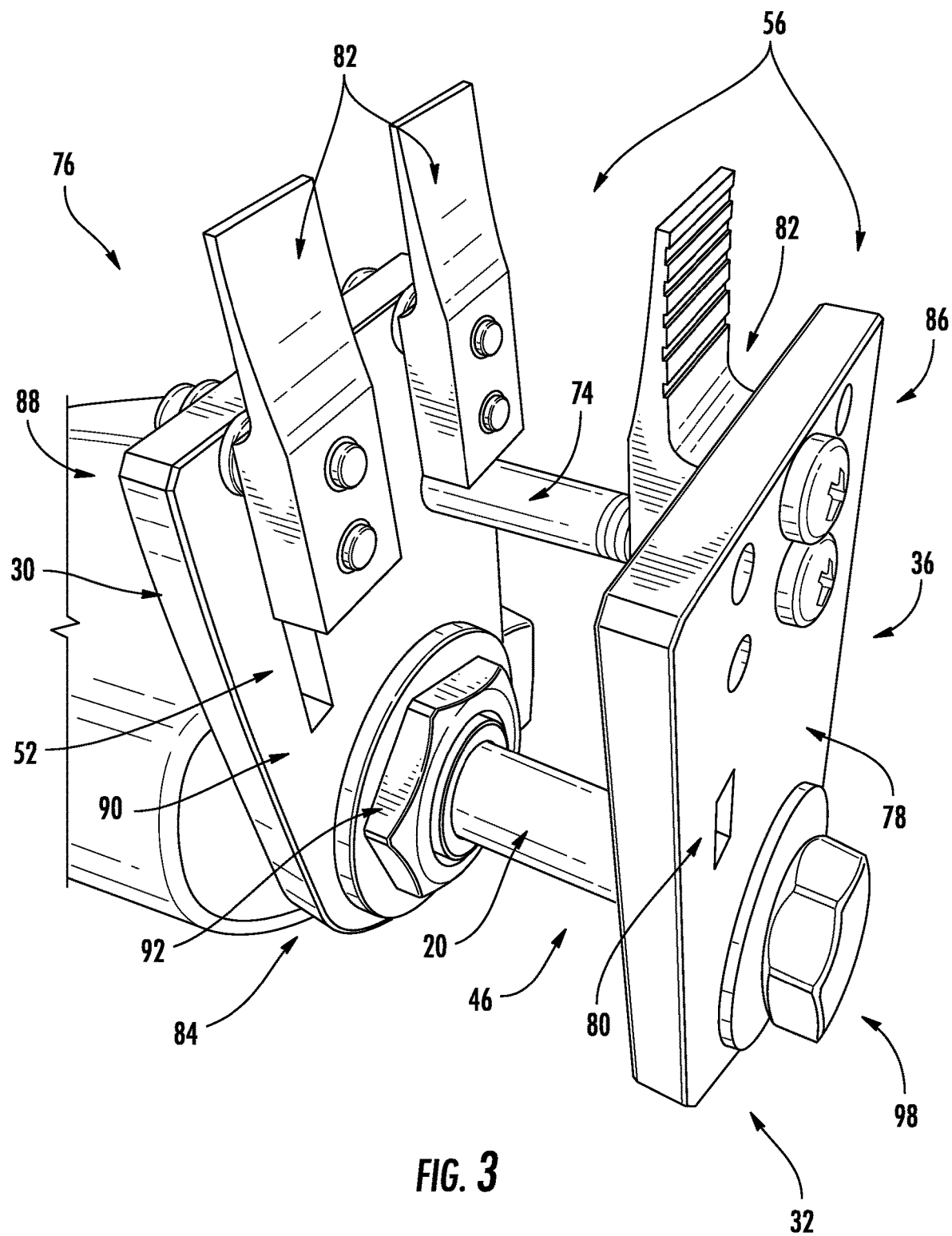
FIG. 3 illustrates a perspective front view of a jaws of an orthopedic cast splitter apparatus, in accordance with embodiments of this disclosure.

FIG. 3 illustrates a perspective front view of a jaws 76 of an orthopedic cast splitter apparatus 10, in accordance with embodiments of this disclosure. The jaws 76 of the orthopedic cast splitter 10, having the set of plates 56, may operate by actuation of the drive rod 20. In some embodiments, the jaws 76 may have a set of teeth 82 coupled adjacent a second end 88 of the fixed plate 30 and a second end 86 of the advance plate 36. The set of teeth 82 may be coupled to the set of plates 56 by a variety of fasteners, e.g., screws, bolts, rivets, or any fasteners. The set of plates 56 may have any number of teeth, e.g., 1, 2, 3, or any number of teeth. In some embodiments, the set of teeth 82 may be formed concomitantly to the set of plates 56. In other embodiments, the set of teeth 82 may be congruent, e.g., having the same shape and size. In further embodiments, the set of teeth 82 may be dissimilar, e.g., having varying shape or size. Although embodiments herein depict an inverse teeth configuration, any configuration may be incorporated. As shown in FIG. 3 (and previously described herein), the second end 46 of the drive rod 20 may protrude through the first opening 28 of the first end 84 of the fixed plate 30, and the second end 46 of the drive rod 20 may continue through the first end 32 of the advance plate 36 and be coupled to the outside surface 78. According to some embodiments, the second end 46 of the drive rod 20 may be coupled to the outside surface 78 of the advance plate 36 by a cap nut 98. The cap nut 98, may be any type or shape of nut, e.g., hexagonal, flanged, acorn, or any type or shape. In even further embodiments, the second end 46 of the drive rod 20 may be coupled to the advance plate 36 by any other coupling methods as known in the art. Encircling the drive rod 20 and coupled to an inner surface 90 of the fixed plate 30 may be a threadless nut 92. The threadless nut 92 may be any shape nut, e.g., hexagonal, square, flange, or any shape. It is envisioned, the threadless nut 92 may be optimized to hold the first actuator spring 42 in position for proper function of the trigger handle 14 while providing optimal axial movement of the drive rod 20.

Figure 4A:
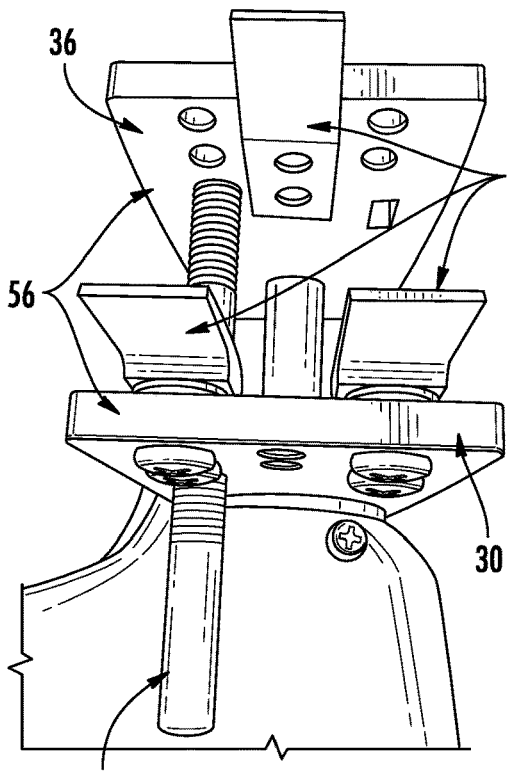
FIG. 4A illustrates a perspective top view of a jaws of an orthopedic cast splitter apparatus, in accordance with embodiments of this disclosure.

FIG. 4A illustrates a perspective top view of a jaws 76 of an orthopedic cast splitter apparatus 10, in accordance with embodiments of this disclosure.

Figure 4B:
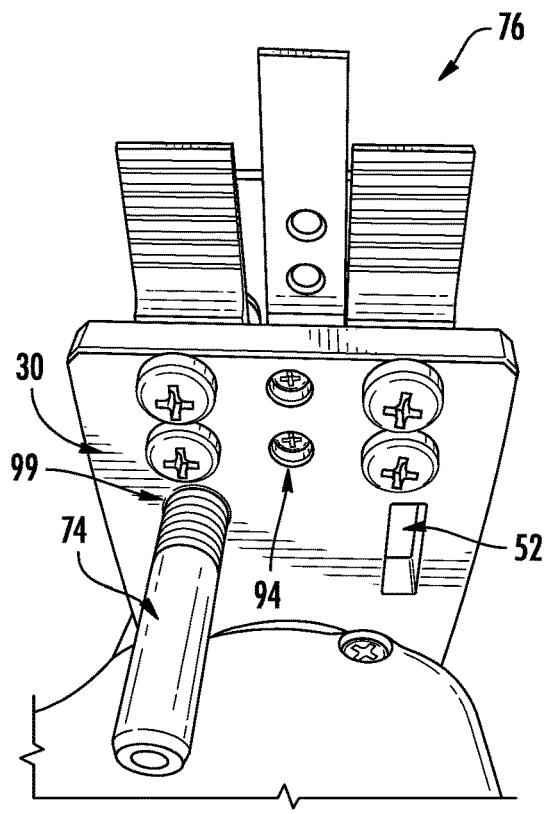
FIG. 4B illustrates a perspective rear view of a jaws of a left facing orthopedic cast splitter apparatus, in accordance with embodiments of this disclosure.

FIG. 4B illustrates a perspective rear view of a jaws 76 of a left facing orthopedic cast splitter apparatus 10, in accordance with embodiments of this disclosure.

Figure 4C:
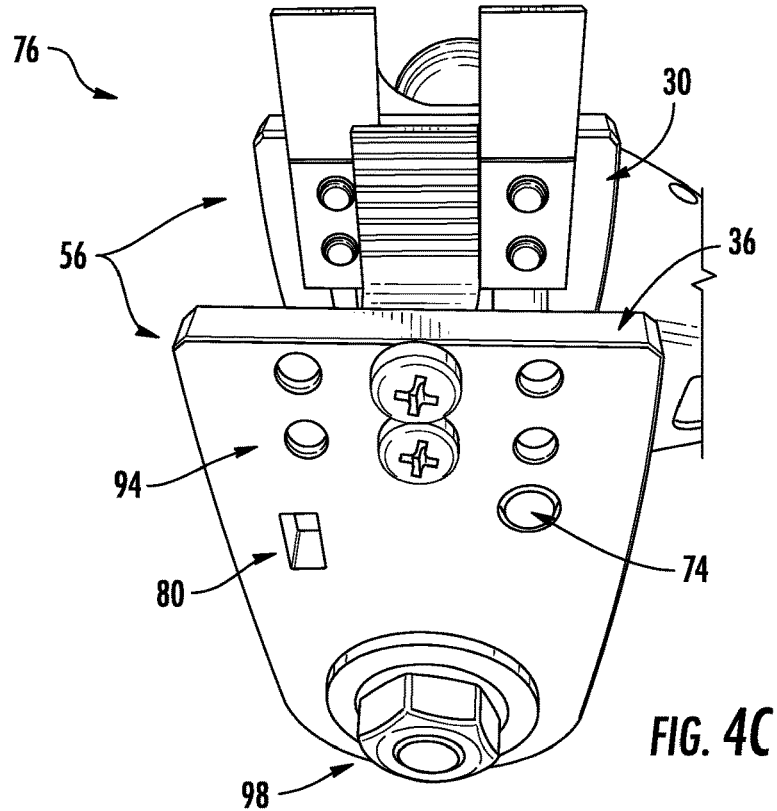
FIG. 4C illustrates a perspective front view of a jaws of a left facing orthopedic cast splitter apparatus, in accordance with embodiments of this disclosure.

FIG. 4C illustrates a perspective front view of a jaws 76 of a left facing orthopedic cast splitter apparatus 10, in accordance with embodiments of this disclosure. Referring to FIG. 4A-FIG. 4C, the alignment bar 74 may be positioned within the jaws 76 and extend from the advance plate 36 through a third opening 99 in fixed plate 30 for a sufficient distance to promote uniform movement of advance plate 36 from fixed plate 30 of the set of plates 56. In some embodiments, the alignment bar 74 may be threaded and secured to advance plate 36. In further embodiments, the alignment bar 74 may be coupled to advance plate 36 by other methods known in the art. The notch 80 within the advance plate 36 and the second opening 52 within the fixed plate 30 may be optimized for slide bar 50 (see FIG. 1). In some embodiments, the slide bar 50 may be used simultaneously or independently of alignment bar 74. Incorporation of both alignment options may be determined by the operator on a case by case basis and may be removed or added accordingly. In other embodiments, the set of plates 56 may have a set of pre-drilled holes 94 for affixing teeth. It is envisioned that the set of teeth 82 may have any configuration suitable for optimized cast splitting, wherein teeth may be added, removed, or replaced. Although embodiments herein depict a maximum of 6 teeth within the set of teeth 82 (as determined by the pre-drilled holes), it is envisioned with variations in shape, size, or configuration, more or less teeth may be determined optimal.

Figure 5:
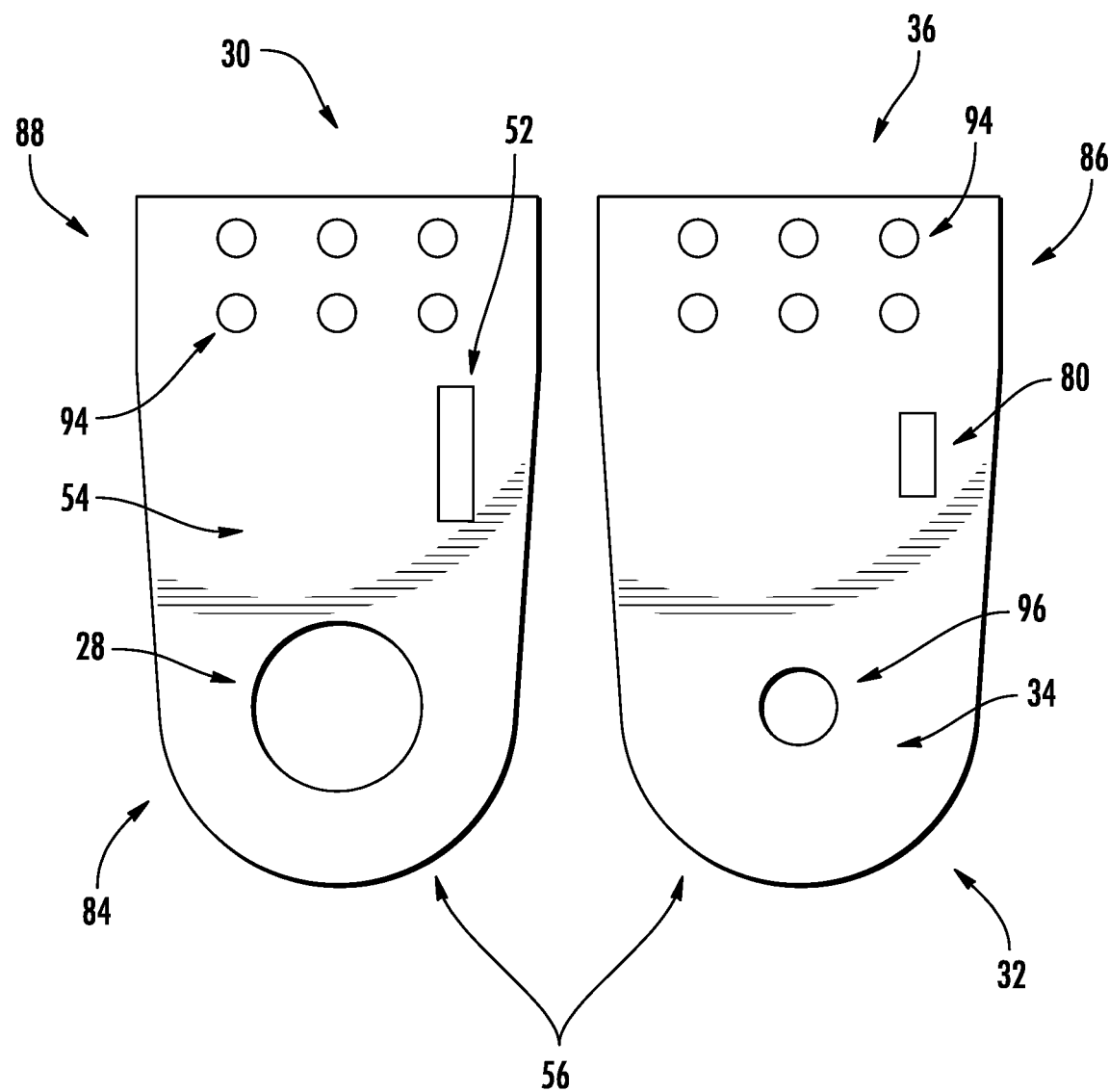
FIG. 5 illustrates a perspective rear view of a set of plates, in accordance with embodiments of this disclosure.

FIG. 5 illustrates a perspective rear view of a set of plates 56, in accordance with embodiments of this disclosure. For orientation, FIG. 5 depicts the outside surface 54 of fixed plate 30 on the left, and inside surface 34 of advance plate 36 on the right. The first opening 28 of the fixed plate 30 may be positioned near or at the first end 84. The first opening 28 may be optimized to house the first actuator spring 42 about the drive rod 20 held in place by threadless nut 92. A first opening 96 of the advance plate 36, positioned near or at the first end 32, may accommodate the second end 46 of the drive rod 20. The second opening 52 of the fixed plate 30 and notch 80 of the advance plate 36 may receive slide bar 50. The notch 80 may span the depth of advance plate 36 as depicted herein as a through hole. In other embodiments, the notch 80 may be a surface indentation. The set of plates 56 each may have pre-drilled holes 94 across the second end 88 and the second end 86 of the fixed plate 30 and the advance plate 36, respectively. Although pre-drilled holes 94 are depicted as pairs, teeth may be coupled using any number of pre-drilled holes or fasteners, e.g., 1, 2, 3, or any other number of pre-drilled holes or fasteners. In other embodiments, the pre-drilled holes 94 may be absent, as teeth may either be formed concomitantly with the set of plates 56 or teeth may be fastened by methods not requiring pre-drilled holes 94.

Figure 6A:
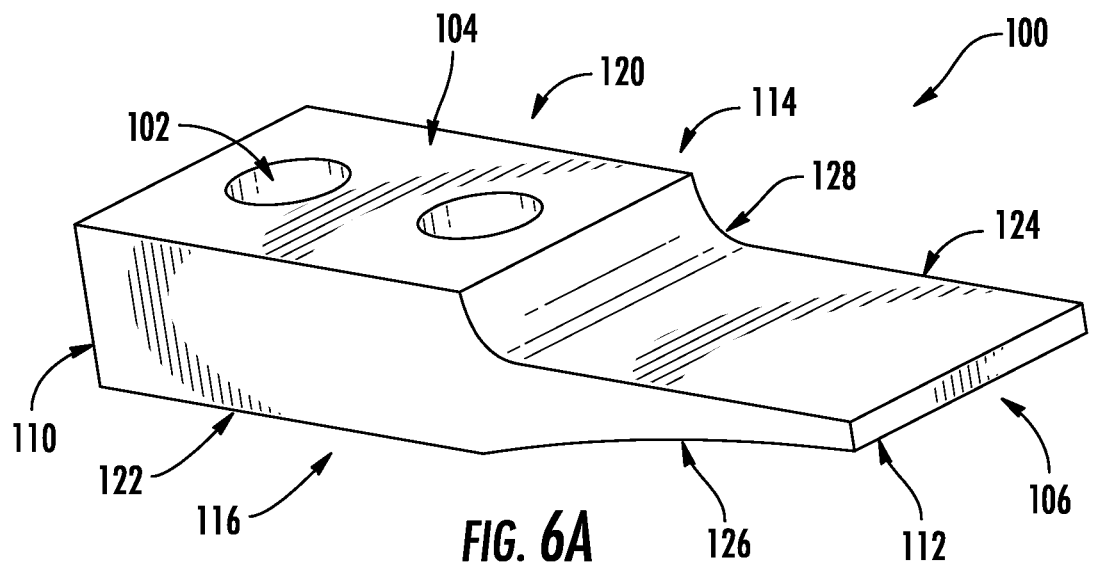
FIG. 6A illustrates a perspective top view of a tooth of a set of teeth, in accordance with embodiments of this disclosure.

FIG. 6A illustrates a perspective bottom view of a tooth 100 of a set of teeth 82, in accordance with embodiments of this disclosure.

Figure 6B:
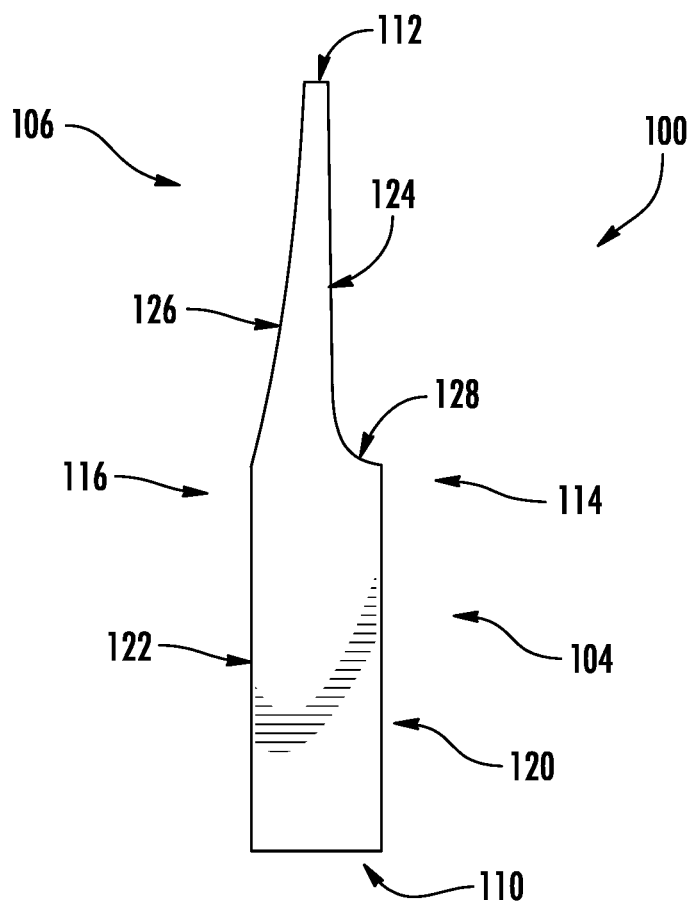
FIG. 6B illustrates a side elevation view of a tooth of a set of teeth, in accordance with embodiments of this disclosure.

FIG. 6B illustrates a side elevation view of a tooth 100 of a set of teeth 82, in accordance with embodiments of this disclosure. Referring to FIGS. 6A and 6B, a tooth 100 is one of a set of teeth 82. The tooth 100 depicted herein, has a set of pre-drilled holes 102 congruent with pre-drilled holes 94 of the set of plates 56. As shown, the tooth 100 may have a first end 110 and a second end 112 disposed opposite one another, and a first side 114 and a second side 116 disposed opposite one another. The tooth 100 may include a base portion 104 extending from the first end 110 and a tip portion 106 extending from the second end 112 to the base portion 104. When removably coupled to the plates 30, 36, the base portion 104 may be disposed between the fixed plate 30 and the advance plate 36, while the tip portion 106 may extend beyond the ends 86, 88 of the plates 30, 36. As shown, the base portion 104 may include a first planar surface 120 and a second planar surface 122 disposed opposite one another and extending parallel to one another. The tip portion 106 may include a third planar surface 124 and a first curved surface 126 disposed opposite one another. The third planar surface 124 may extend parallel to the first planar surface 120 and the second planar surface 122 and may be configured to engage the orthopedic cast along the fissure. The first curved surface 126 may be configured to ease insertion within the fissure. As shown, the tip portion also may include a second curved surface 128 disposed to provide a transition between the first planar surface 120 and the third planar surface 124. The first planar surface 120 may be optimized to be contiguous with the inside surfaces of the set of plates 56 (not shown). The second end 112 of tooth 100 may be tapered and optimized to effectively be inserted within a fissure of an orthopedic cast to be split. In some embodiments the second end 112 may taper to a sharpened end. In other embodiments, the second end 112 may taper to a blunt end. In further embodiments, the second end 112 may taper to an end of any shape, e.g., square, spiked, scalene, or any shape.

Figure 7A:
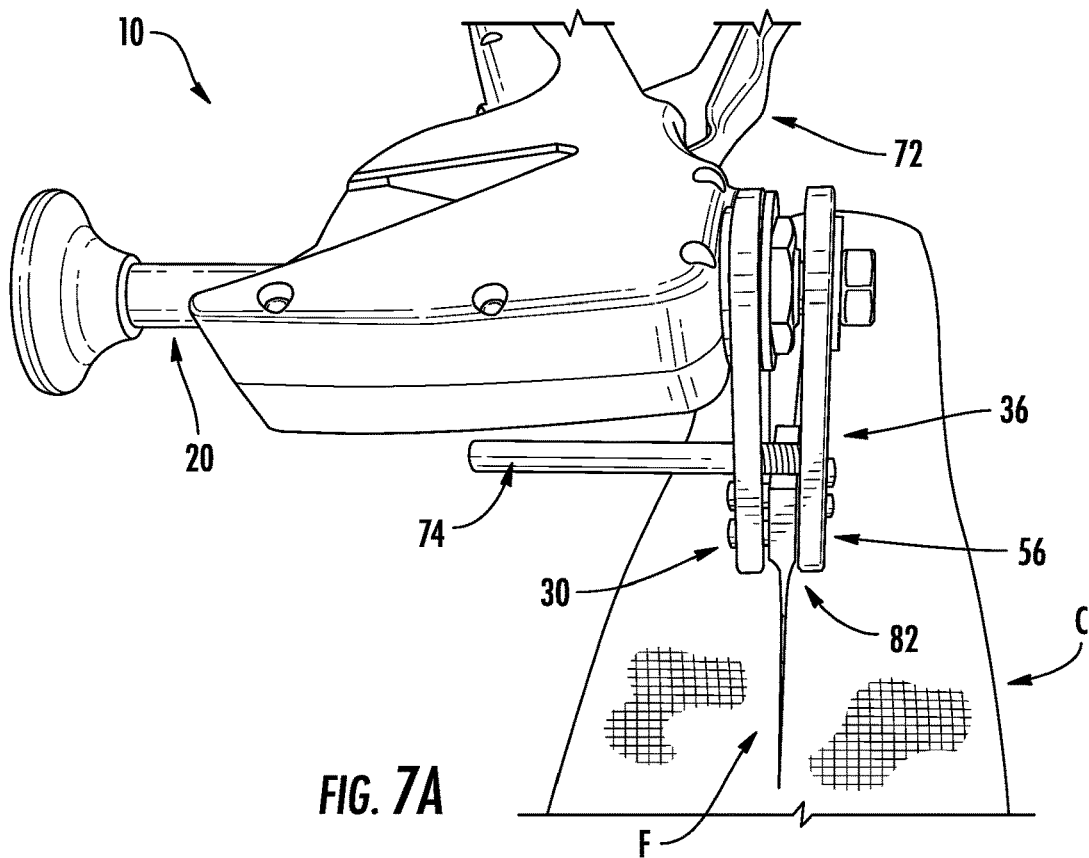
FIG. 7A illustrates a top view of an inserted orthopedic cast splitter apparatus in a closed position, in accordance with embodiments of this disclosure.

FIG. 7A illustrates a top view of an inserted orthopedic cast splitter apparatus 10 in a closed position, in accordance with embodiments of this disclosure.

Figure 7B:
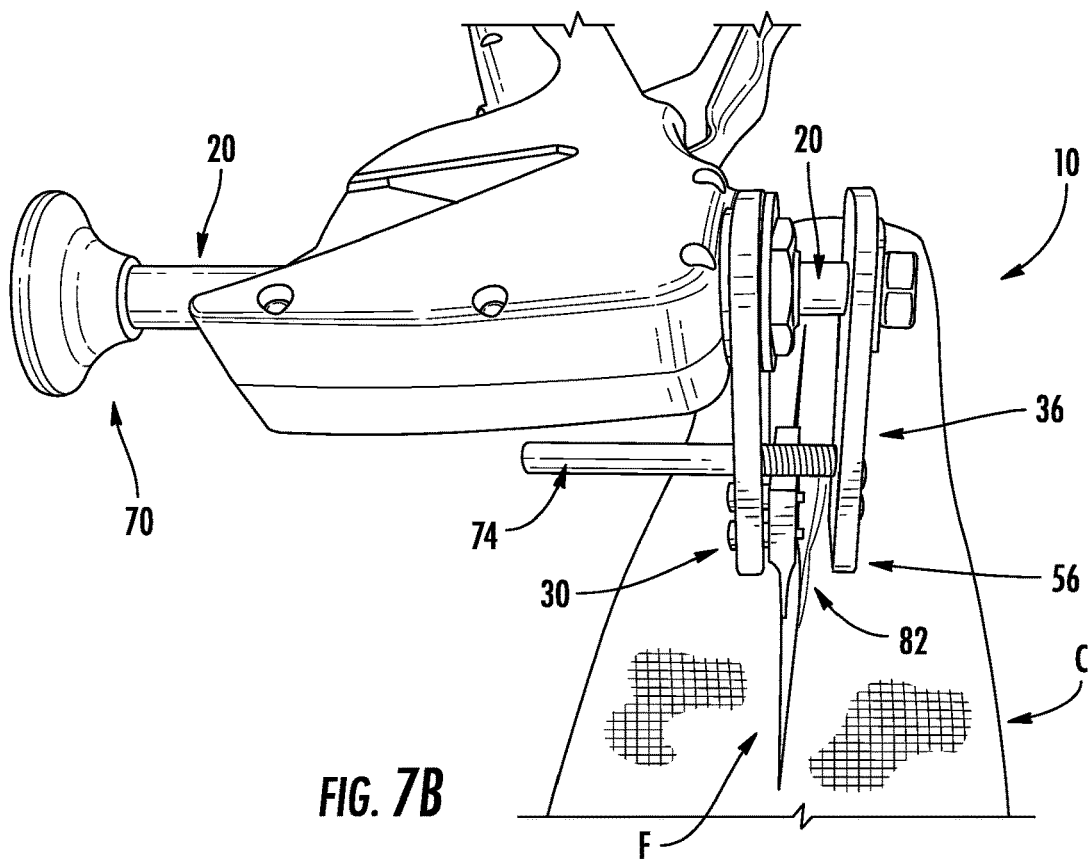
FIG. 7B illustrates a top view of an inserted orthopedic cast splitter apparatus actuating splitting of an orthopedic cast, in accordance with embodiments of this disclosure.

FIG. 7B illustrates a top view of an inserted orthopedic cast splitter apparatus 10 actuating splitting of an orthopedic cast C, in accordance with embodiments of this disclosure. Referring to FIGS. 7A and 7B, the set of teeth 82 adjacent the set of plates 56 may be inserted within a fissure F of an orthopedic cast C while in a closed position, in which the set of plates 56 may be abutting (FIG. 7A). Once the set of teeth 82 are sufficiently within the fissure, actuation of the lock and release trigger handle 72 may begin. With one hand, the operator may squeeze the lock and release trigger handle 72 toward the frame, actuating the drive rod 20 effecting movement of advance plate 36 in the forward axial direction (away from fixed plate 30). The operator may subsequently loosen the grip of the lock and release trigger handle 72 without losing progression of the advance plate 36. Continued actuation of the drive rod 20 by repeatedly squeezing the lock and release trigger handle 72, may incrementally move the advance plate 36 away from fixed plate 30, increasing the size of the fissure F within the orthopedic cast C (FIG. 7B). Further actuation of the drive mechanism effecting movement in the forward axial direction will continue to open the orthopedic cast ultimately resulting in orthopedic cast C splitting.

Various modifications and additions can be made to the exemplary embodiments discussed without departing from the scope of the disclosed subject matter. For example, while the embodiments described above refer to particular features, the scope of this disclosure includes embodiments having different combinations of the features and embodiments that do not include all of the described features. Accordingly, the scope of the disclosed subject matter is intended to embrace all such alternatives, modifications, and variations as fall within the scope of the claims, together with all equivalents thereof.

In some embodiments, the respective features of the orthopedic cast splitter apparatus 10 and the components thereof may have the relative dimensional relationships depicted in FIGS. 1-7B. Various other suitable relative dimensional relationships between respective features of the orthopedic cast splitter apparatus 10 and the components thereof may be used in other embodiments.

Although specific embodiments of the disclosure have been described, one of ordinary skill in the art will recognize that numerous other modifications and alternative embodiments are within the scope of the disclosure. For example, while various illustrative implementations and structures have been described in accordance with embodiments of the disclosure, one of ordinary skill in the art will appreciate that numerous other modifications to the illustrative implementations and structures described herein are also within the scope of this disclosure.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments.

What is claimed is:

1. An orthopedic cast splitter apparatus for splitting an orthopedic cast, the orthopedic cast splitter apparatus comprising:
   a frame;
   a handle pivotally coupled to the frame;
   a drive rod configured to translate relative to the frame; and
   jaws comprising:

a first plate coupled to the frame;
a second plate coupled to the drive rod and extending parallel to the first plate, the second plate configured to translate relative to the first plate;
a first tooth removably coupled to the first plate and extending beyond an end of the first plate, the first tooth configured to be inserted within a fissure formed in the orthopedic cast; and
a second tooth removably coupled to the second plate and extending beyond an end of the second plate, the second tooth configured to be inserted within the fissure.

2. The orthopedic cast splitter apparatus of claim 1, wherein the handle is configured to pivot within a central plane defined by the frame, wherein the first plate extends in a lateral direction perpendicular to the central plane, wherein the second plate extends in the lateral direction, wherein the first plate extends in the lateral direction beyond an end of the first plate, and wherein the second plate extends in the lateral direction beyond an end of the second plate.

3. The orthopedic cast splitter apparatus of claim 1, wherein the first tooth is removably coupled to the first plate via one or more first fasteners extending through one or more holes defined in the first tooth and one or more holes defined in the first plate, and wherein the second tooth is removably coupled to the second plate via one or more second fasteners extending through one or more holes defined in the second tooth and one or more holes defined in the second plate.

4. The orthopedic cast splitter apparatus of claim 1, wherein the first plate is rigidly coupled to the frame, and wherein the second plate is rigidly coupled to the drive rod.

5. The orthopedic cast splitter apparatus of claim 1, wherein the first tooth and the second tooth each comprise:
a base portion disposed between the first plate and the second plate, the base portion comprising a first planar surface and a second planar surface disposed opposite one another and extending parallel to one another; and
a tip portion extending beyond the end of the first plate and the end of the second plate, the tip portion comprising a third planar surface and a curved surface disposed opposite one another, the third planar surface extending parallel to the first planar surface and the second planar surface and configured to engage the orthopedic cast along the fissure, the curved surface configured to ease insertion within the fissure.

6. The orthopedic cast splitter apparatus of claim 5, wherein the third planar surface of the first tooth is disposed opposite the third planar surface of the second tooth, and wherein the curved surface of the first tooth is disposed opposite the curved surface of the second tooth.

7. The orthopedic cast splitter apparatus of claim 1, wherein the jaws is configured to move between a closed position, in which the first tooth and the second tooth are aligned with one another in a common plane, and an open position in which the first tooth and the second tooth are spaced apart from one another in a direction perpendicular to the common plane.

8. The orthopedic cast splitter apparatus of claim 7, wherein the jaws further comprises a third tooth removably coupled to the first plate or the second plate, and wherein the third tooth is aligned with the first tooth and the second tooth in the common plane when the jaws is in the closed position.

9. The orthopedic cast splitter apparatus of claim 1, further comprising a bar extending parallel to the drive rod and configured to maintain an orientation of the second plate relative to the first plate as the second plate translates relative to the first plate.

10. The orthopedic cast splitter apparatus of claim 9, wherein the bar is coupled to the drive rod, and wherein the bar engages an opening defined in the first plate and an opening defined in the second plate.

11. The orthopedic cast splitter apparatus of claim 9, wherein the bar is rigidly coupled to the second plate, and wherein the bar engages an opening defined in the first plate.

12. An orthopedic cast splitter apparatus for splitting an orthopedic cast, the orthopedic cast splitter apparatus comprising:
a frame;
a handle pivotally coupled to the frame and configured to pivot within a central plane defined by the frame;
a drive rod configured to translate relative to the frame; and
jaws comprising:
a first plate coupled to the frame and extending in a lateral direction perpendicular to the central plane;
a second plate coupled to the drive rod and extending in the lateral direction, the second plate configured to translate relative to the first plate;
a first tooth coupled to the first plate and extending in the lateral direction beyond an end of the first plate, the first tooth configured to be inserted within a fissure formed in the orthopedic cast; and
a second tooth coupled to the second plate and extending in the lateral direction beyond an end of the second plate, the second tooth configured to be inserted within the fissure.

13. The orthopedic cast splitter apparatus of claim 12, wherein the first plate is rigidly coupled to the frame, wherein the second plate is rigidly coupled to the drive rod, wherein the first tooth is removably coupled to the first plate, and wherein the second tooth is removably coupled to the second plate.

14. The orthopedic cast splitter apparatus of claim 12, wherein the first tooth and the second tooth each comprise:
a base portion disposed between the first plate and the second plate, the base portion comprising a first planar surface and a second planar surface disposed opposite one another and extending parallel to one another; and
a tip portion extending beyond the end of the first plate and the end of the second plate, the tip portion comprising a third planar surface and a curved surface disposed opposite one another, the third planar surface extending parallel to the first planar surface and the second planar surface and configured to engage the orthopedic cast along the fissure, the curved surface configured to ease insertion within the fissure.

15. The orthopedic cast splitter apparatus of claim 12, further comprising a bar extending parallel to the drive rod and configured to maintain an orientation of the second plate relative to the first plate as the second plate translates relative to the first plate.

16. The orthopedic cast splitter apparatus of claim 15, wherein the bar is coupled to the drive rod, and wherein the bar engages an opening defined in the first plate and an opening defined in the second plate.

17. The orthopedic cast splitter apparatus of claim 15, wherein the bar is rigidly coupled to the second plate, and wherein the bar engages an opening defined in the first plate.

18. A method for splitting an orthopedic cast, the method comprising:

providing an orthopedic cast splitter apparatus comprising:
- a frame;
- a handle pivotally coupled to the frame and configured to pivot within a central plane defined by the frame;
- a drive rod configured to translate relative to the frame; and
- a jaws comprising:
    - a first plate coupled to the frame and extending in a lateral direction perpendicular to the central frame;
    - a second plate coupled to the drive rod and extending in the lateral direction, the second plate configured to translate relative to the first plate;
    - a first tooth coupled to the first plate and extending in the lateral direction beyond an end of the first plate; and
    - a second tooth coupled to the second plate and extending in the lateral direction beyond an end of the second plate;

inserting the first tooth and the second tooth within a fissure formed in the orthopedic cast; and pivoting the handle relative to the frame such that the second plate translates relative to the first plate, thereby increasing a size of the fissure.

19. The method of claim 18, wherein the first tooth is removably coupled to the first plate, and wherein the second tooth is removably coupled to the second plate.

20. The method of claim 18, further comprising maintaining, via a bar of the orthopedic cast splitter apparatus extending parallel to the drive rod, an orientation of the second plate relative to the first plate as the second plate translates relative to the first plate.

* * * * *